United States Patent [19]
Lingwood et al.

[11] Patent Number: 6,103,883
[45] Date of Patent: Aug. 15, 2000

[54] GLYCOLIPID MIMICS AND METHODS OF USE THEREOF

[75] Inventors: Clifford A. Lingwood; Murugesapillai Mylvaganam, both of Toronto, Canada

[73] Assignee: HSC Research and Development Limited Partnership, Toronto, Canada

[21] Appl. No.: 09/340,705

[22] Filed: Jun. 29, 1999

Related U.S. Application Data

[63] Continuation of application No. 08/753,222, Nov. 22, 1996, Pat. No. 5,973,128.

[51] Int. Cl.$^7$ .......................... C07H 15/00; C07H 17/00; A61K 31/70
[52] U.S. Cl. .................. 536/4.1; 536/17.2; 536/18.7; 536/123.1; 536/17.9; 514/25; 514/54
[58] Field of Search ..................................... 536/4.1, 17.2, 536/17.9, 18.7, 123.1; 514/25, 54

[56] References Cited

U.S. PATENT DOCUMENTS

| | | | |
|---|---|---|---|
| 4,359,460 | 11/1982 | Nair et al. | 424/180 |
| 4,859,769 | 8/1989 | Karlsson et al. | 536/53 |
| 4,868,289 | 9/1989 | Magnusson et al. | 536/4.1 |
| 5,164,298 | 11/1992 | Lingwood et al. | 435/7.37 |
| 5,242,800 | 9/1993 | Jimenez et al. | 435/7.2 |
| 5,399,567 | 3/1995 | Platt et al. | 514/315 |
| 5,449,608 | 9/1995 | Young et al. | 435/7.2 |

FOREIGN PATENT DOCUMENTS

| | | |
|---|---|---|
| 0433112 | 6/1991 | European Pat. Off. |
| 0516851 | 12/1992 | European Pat. Off. |
| WO 8603971 | 7/1986 | WIPO |

OTHER PUBLICATIONS

Ono et al. *Chemistry Letters* 1991, 3, 395–398. month not available.

Nagai et al. *Bull. Chem. Soc. Jpn.* Oct. 1993, 66(10), 2965–2971.

Lingwood, C.A. "Verotoxins and Their Glycolipid Rececptors" *Advances in Lipid Research* 25:189–211.

Berge et al. "Pharmaceutical Salts" *Journal of Pharmaceutical Sciences* 66(1):1–19 (Jan. 1977).

Boyd, B. et al. "Lipid modulation of glycolipid receptor function. Availability of Gal($\alpha$1–4)Gal disaccharide for verotoxin binding in natural and synthetic glycolipids" *Eur. J. Biochem.* 223:873–878 (1994).

Fenderson, B.A. et al. "Glycoconjugate expression during embryogenesis and its biological significance" *BioEssays* 12(4):173–179 (Apr. 1990).

Hakomori, S. "Bifunctional role of glycosphingolipids" *The Journal of Biological Chemistry* 265(31):18713–18716 (Nov. 1990).

Hakomori, S. et al. "Glycosphingolipids as tumor–associated and differentiation markers" *Journal ot the National Caner Institute (JNCI)* 71(2):231–251 (Aug. 1983).

Kiarash, A. et al. "Glycosphingolipid receptor function is modified by fatty acid content. Verotoxin 1 and Verotoxin 2c preferentially recognize different globotriaosyl ceramide fatty acid homologues" *the Journal of Biological Chemistry* 269(15):11138–11146 (Apr. 1994).

Kundu, S.K. et al. "Aminopropyl silica gel as a solid support for preparation of glycolipid immunoadsorbent and purification of antibodies" *Journal of Lipid Research* 20:825–833 (1979).

Laine, R. et al. "Glycosphingolipids covalently liked to agarose gel or glass beads" *The Journal of Biological Chemistry* 249(14):4460–4466 (Jul. 1974).

Lingwood, C. et al. "Synthesis and use of galactolipid sulfotransferase substrate–analogue affinity probes: possible localization of the testicular enzyme" *Biochem. Cell Biol.* 64:631–637 (1986).

MacDonald, D.L. et al. "Notes on improved procedure for the chemical modification and degradation of glycosphinglipids" *Journal of Lipid Researcj* 21:642–645 (1980).

Pagano, R. et al. "A series of fluorescent N–acylsphingosines: synthesis, physical properties, and studies on cultured cells" *Biochemistry* 27:4439–4445 (1988).

Pellizzari, A. et al. "Binding of Verocytotoxin 1 to its receptor is influenced by differences in receptor fatty acid content" *Biochemistry* 31:1363–1370 (1992).

Sakac, D. et al. "Purification of the testicular galactolipid: 3'–phosphoadenosine 5' phosphosulfate sulfotransferase" *The Journal of Biological Chemistry* 267(3):1655–1659 (Jan. 1992).

Sonnino, S. et al. "Preparation of GM1 ganglioside molecular species having homogeneous fatty acid and long chain base moieties" *Journal of Lipid Research* 26:248–257 (1985).

*Primary Examiner*—Kathleen K. Fonda
*Attorney, Agent, or Firm*—Lahive & Cockfield, LLP; Giulio A. DeConti, Jr.; Nicholas P. Triano, III

[57] ABSTRACT

Glycolipid mimics which include a rigid hydrophobic moiety are disclosed. Methods of using the glycolipid mimics are also disclosed.

11 Claims, 7 Drawing Sheets

M = LEWIS ACID METAL CENTER e.g., $Zn^{2+}$

GLYCOLIPID MIMICS AND METHODS OF USE THEREOF

This application is a continuation application of Ser. No. 08/753,222 filed on Nov. 22, 1996, now U.S. Pat. No. 5,973, 128. The contents of all of the aforementioned application are hereby incorporated by reference.

BACKGROUND OF THE INVENTION

Glycosphingolipids (GSL) form a unique amphipathic subclass of glycoconjugates present on the external leaflet of the eukaryote plasma membrane. A variety of functions have been ascribed to glycolipids including intercellular recognition (1), growth regulation (2), differentiation (3) and microbial adhesion.

GSLs have been studied by isolation of purified GSLs and subsequent chemical modifications. An example of such a chemical transformation is the synthesis of deacyl-GSLs, in which GSL function has been investigated by coupling the free amine functionality of the sphingosine to various molecular units, including fatty acids (4–7), cross linkers (7) or fluorescent probes (8, 9). Similarly, although to a lesser extent, some effort has been directed towards the oxidative cleavage of the internal double bond of the sphingosine (10), where the allylic alcohol component of the ceramide is transformed into a α-hydroxycarboxylate function.

It has been recognized, however, that isolated soluble GSLs do not always retain the binding characteristics of the membrane-bound glycolipid. In fact, solubilized GSLs may have little or no binding affinity for compounds which bind strongly to the membrane-bound GSL. For example, verotoxin, a toxin produced by certain pathogenic bacteria, binds to globotriaosyl ceramide ($Gb_3$), a GSL which is anchored in the cell membrane by two long, hydrophobic hydrocarbon chains. However, the binding of verotoxin to $Gb_3$ which has been freed from the membrane is much weaker.

The ability to study interactions between GSLs and compounds or pathogens which bind to GSLs, in the solution phase, therefore requires glycolipid mimics which are soluble, yet retain the binding affinity of membrane-bound naturally-occurring GSLs for toxins and pathogens.

SUMMARY OF THE INVENTION

The present invention relates to glycolipid mimics, pharmaceutical compositions of the glycoprotein mimics, and methods for making and using the glycoprotein mimics.

In one aspect, the invention provides a glycolipid mimic which retains as least one binding property of a naturally-occurring glycolipid. In one embodiment, the glycolipid mimic is represented by the formula A-B-C, in which A is a saccharide moiety, B is absent or, if present, is a linker moiety, and C is a rigid hydrophobic moiety. In general, the moieties A, B, and C are selected such that the glycolipid mimic is soluble and retains at least one binding property of a membrane-bound naturally-occurring glycolipid. In certain embodiments, the glycolipid mimic can be represented by the formula A-B-C-D, in which A, B, and C are as described above, and D is a carrier moiety, or a solid support or a linker to a solid support. In this embodiment, D can be, e.g., a carrier suitable for promoting an immunogenic response to the glycolipid mimic, i.e., such that the glycolipid mimic A-B-C-D is useful as a vaccine.

In another aspect, the invention provides a pharmaceutical composition. The pharmaceutical compositions comprises a therapeutically effective amount of a glycolipid mimic of the invention, or a pharmaceutically acceptable salt thereof, and a pharmaceutically acceptable carrier.

In yet another embodiment, the invention provides a method for preparing a glycolipid mimic having a rigid hydrophobic moiety. The method includes the steps of providing a glycolipid or glycolipid analog having at least one functional group capable of being coupled with a rigid hydrophobic moiety, and coupling the glycolipid or glycolipid analog with a rigid hydrophobic moiety, there by preparing the glycolipid mimic having a rigid hydrophobic moiety.

In still another aspect, the invention provides a method for inhibiting the binding of a toxin or a pathogen to a host cell. The method includes the step of contacting the toxin or pathogen, or the host cell, with a glycolipid mimic in an amount sufficient to inhibit the binding of the toxin or pathogen to the host cell, thereby inhibiting the binding of the toxin or pathogen to the host cell. The method includes the further step of contacting the host cell with the toxin or pathogen. The method is useful for inhibiting the binding of a toxin or pathogen to a host cell either in vitro or in vivo. In certain preferred embodiments, the pathogen is selected from the group consisting of bacterial, fungi, and viruses. In certain embodiments, the toxin is verotoxin.

In yet another aspect, the invention provides a method for detecting the presence or absence of a pathogen in a sample. The method includes the steps of contacting the sample with a glycolipid mimic, and measuring the binding of a pathogen, if present, to the glycolipid mimic, thereby detecting the presence or absence of the pathogen. In a preferred embodiment, the glycolipid mimic is immobilized to a solid support. In certain preferred embodiments, the pathogen is selected from the group consisting of bacterial, fungi, and viruses.

In still another embodiment, the invention provides a method for isolating components of a pathogen which mediate pathogen attachment to a host cell. The method includes the steps of contacting a sample containing a pathogen (or a component of a pathogen) with a glycolipid mimic, and isolating a component of the pathogen which binds to the glycolipid mimic, such that a component of the pathogen which mediates pathogen attachment to a host cell is isolated.

DETAILED DESCRIPTION OF THE INVENTION

The present invention relates to glycolipid mimics, pharmaceutical compositions of the glycoprotein mimics, and methods for making and using the glycoprotein mimics. The compounds of the invention are useful as receptor analogs for studying the interaction between toxins and pathogens which bind to glycolipid receptors.

In one aspect, the invention provides a glycolipid mimic which retains as least one binding property of a naturally-occurring glycolipid. In one embodiment, the glycolipid mimic is represented by the formula A-B-C, in which A is a saccharide moiety, B is absent or, if present, is a linker moiety, and C is a rigid hydrophobic moiety.

The saccharide moiety A can be a saccharide moiety of a naturally-occurring glycolipid, or a derivative or analog thereof. For example, verocytotoxin binds to globotriaosyl ceramide ($Gb_3$) (see, e.g., U.S. Pat. No. 5,164,298 to Lingwood et al., and references cited therein), which includes a saccharide portion having the structure Gal(alpha 1–4)Gal (beta 1–4)Glc, in which Gal represents a galactosyl residue and Glc represents a glucosyl residue. Thus, the saccharide moiety A of the glycolipid mimic of the invention can be Gal(alpha 1–4)Gal(beta 1–4)Glc. Other saccharides are known which bind to other toxins (see, e.g., U.S. Pat. No. 5,399,567 to Platt et al., and references cited therein). Other saccharides are known to be specifically recognized by a variety of pathogens, including fungi, bacteria, and viruses (see, e.g., U.S. Pat. No. 5,399,567 to Platt et a., U.S. Pat. No. 5,449,608 to Young and Brown; U.S. Pat. No. 4,859,769 to Karlsson et al.; and references cited therein). Accordingly, glycolipid mimics having appropriate saccharide moieties can be prepared, e.g., by the methods described herein, and used, e.g., to inhibit binding of a toxin or pathogen to a receptor, e.g., a glycolipid receptor present in the membrane of a host cell. In preferred embodiments, the saccharide moiety A comprises a disaccharide, a trisaccharide, or a tetrasaccharide. It will be appreciated by the ordinarily skilled artisan that derivatives and analogs of naturally-occurring saccharides can be used in the compounds of the invention, provided that the derivatives or analogs retain at least one binding characteristic of a membrane-bound glycolipid.

In certain embodiments, the moiety B is absent, i.e., the saccharide moiety A is directly linked to the hydrophobic moiety C, preferably through a covalent bond. For example, a hydroxyl group of the saccharide moiety A can be covalently linked to a hydrophobic moiety C by formation of an ester or ether bond. In preferred embodiments, the moiety B is present and is a linking moiety which joins the saccharide moiety A with the hydrophobic moiety C. The linking moiety B can be, e.g., an alkylene, alkenylene, alkynylene, cycloalkylene, or arylene moiety (preferably a lower alkylene, lower alkenylene or lower alkynylene), which can be unsubstituted or substituted with, e.g., alkyl, aryl, amino, alkylamino, dialkylamino, acylamino, hydroxyl, halogen, or other substituents. The backbone of the moiety B can also comprise, e.g., an ether functionality, a thioether functionality, an amino functionality, an amido functionality, or the like. In general, B is selected such that the glycolipid mimic is soluble, e.g., in aqueous solution, and retains at least one binding characteristic of a membrane-bound glycolipid. For example, B is selected such that a toxin or pathogen can bind to the glycolipid mimic. In a preferred embodiment, B is a fragment of a glycolipid, or a derivative or analog thereof, which, in certain more preferred embodiments, comprises a long-chain hydrocarbyl chain (e.g., having at least eight carbon atoms in the chain). For example, in the Examples described below, B is a fragment of a glycolipid obtained by, e.g., deacylation of a GSL, oxidative cleavage of a GSL, or similar chemical transformations.

The hydrophobic moiety C is preferably a rigid moiety which comprises at least one carbocyclic or heterocyclic ring element. The moiety C is selected, in combination with the moieties A and B, such that the glycolipid mimic is soluble, e.g., in aqueous solution, and retains at least one binding characteristic of a membrane-bound glycolipid. In preferred embodiments, the hydrophobic moiety C is sterically bulky, e.g., has a greater effective steric bulk in solution than a long hydrocarbon chain, e.g., $-(CH2)_{11}CH_3$. Without wishing to be bound by any theory, it is believed that the rigidity and/or sterically bulky nature of the C moiety can prevent packing interactions between molecules of the glycolipid mimic in solution and thereby prevent the formation of lipid structures, e.g., lamellar or other lipid vesicles, which are less soluble in water and/or do not exhibit specific binding interactions with toxins or pathogens. Examples of suitable hydrophobic moieties include substituted or unsubstituted hydrocarbons, e.g., adamantyl; or substituted or unsubstituted aromatic compounds such as naphthyl, quinolyl, acridinyl, tetrahydroacridinyl, anthracenyl, benzopyrenyl, and the like. Large hydrophobic moieties such as porphyrins can also be used in the compounds and methods of the invention. Exemplary compounds of the invention are shown in FIG. 2; illustrative moieties which can be used as hydrophobic moieties in the compounds of the invention are shown in FIG. 3. The hydrophobic moiety preferably has a steric bulk greater than the steric bulk of a phenyl group; certain compounds in which C is a phenyl group have been found to be ineffective glycolipid mimics.

The ordinarily skilled artisan will appreciate that substituents on the hydrophobic moiety can be selected to provide for a desired degree of solubility. Thus, for example, a hydrophobic moiety can be substituted, e.g., with a substituent which increases water solubility (e.g., carboxylate, phosphate, sulfonate, sulfate, hydroxyl, amino, and the like); or which decreases water solubility (e.g., substituted or unsubstituted alkyl (including branched alkyl or cycloalkyl)) or increases steric bulk. Other hydrophobic moieties useful in the invention can be selected by the skilled artisan with no more than routine experimentation.

As described above, the moieties A, B, and C are selected such that the glycolipid mimic is soluble and retains at least one binding property of a membrane-bound naturally-occurring glycolipid. In a preferred embodiment, the linking moiety B comprises a fragment of a glycosphingolipid, which fragment includes a nitrogen atom of the GSL, and the hydrophobic moiety C is covalently bonded to the linking moiety B through the nitrogen atom of B (see, e.g., Example 8, below). In this embodiment, it is preferred that the linking moiety B comprises a long-chain hydrocarbyl moiety (e.g., having at least eight carbon atoms in the chain). In certain preferred embodiments, the linking moiety B comprises a fragment of a glycosphingolipid, which fragment includes a nitrogen atom of the GSL, and the hydrophobic moiety C is covalently bonded to the linking moiety B through an atom other than the nitrogen atom of B.

In certain embodiments, the glycolipid mimic can be represented by the formula A-B-C-D, in which A, B, and C are as described above, and D is a carrier moiety, or a solid support or a linker to a solid support. In this embodiment, D can be, e.g., a carrier or adjuvant suitable for promoting an immunogenic response to the glycolipid mimic, i.e., such that the glycolipid mimic A-B-C-D is useful as a vaccine. Such carriers or adjuvants are well known to the ordinarily skilled artisan.

In another embodiment, D is a linker which can immobilize the glycolipid mimic to a solid (or insoluble support).

A variety of linkers are known for immobilization of compounds of interest on a solid support. For example, homo- or hetero-bifunctional cross-linkers can be used to immobilize a glycolipid mimic of the invention on a suitable-functionalized solid support. Many crosslinkers are available commercially, e.g., from Pierce Chemical, Rockford, Ill. The glycolipid mimic can also be immobilized through incorporation of a member of a specific binding pair, e.g., biotin, which can bind to the complementary member of the pair, e.g, avidin or streptavidin. Many such specific binding pairs are known in the art, including hormone/receptor, enzyme/substrate, nucleic acid/complementary nucleic acid, and the like.

Solid supports contemplated for use in the invention, e.g., for performing the assays of the invention, include, for example, beads, e.g., polymeric resin or latex beads; silicon chips or wafers; multiwell plates; culture dishes; silica-based particles, e.g., for use in chromatography; controlled-pore glass; and the like.

The compounds of the invention are useful for overcoming certain difficulties experienced in previous studies of toxin-receptor interactions. For example, as previously described, solubilized glycolipids do not always exhibit the same binding affinity for toxins as do membrane-bound glycolipids. The subject glycolipids maintain at least one binding characteristic of a membrane-bound glycolipid while in solution, thereby enabling studies of the interaction between toxins and glycolipid receptors to be performed in solution.

The term "at least one binding characteristic" as used herein, refers to binding charateristics such as binding affinity, specificity, and the like. Such binding characteristics are readily measured, e.g., by the methods described herein or by known techniques.

Assays suitable for measuring binding of a toxin to a glycolipid are known in the art, and are described, e.g., in B. Boyd et al., *Eur. J Biochem.* 223:873–878 (1994), and in Examples 7 and 8, infra. Thus, the ordinarily skilled artisan can readily make glycolipid mimics, e.g., as described herein, and readily screen the compounds to determine which compounds have the greatest activity. Accordingly, determining which glycolipid compounds of the invention are effective inhibitors of the interaction between a toxin or pathogen and a glycolipid receptor will be routine to one of ordinary skill in the art.

A compound which is "soluble" as used herein, has appreciable solubility in water, or in a solvent which is a mixture of water and a water-miscible solvent, e.g., methanol, ethanol, DMSO, dimethylformamide, and the like, and retains binding activity in solution.

In another aspect, the invention provides a pharmaceutical composition. The pharmaceutical compositions comprise a therapeutically effective amount of a glycolipid mimic of the invention, or a pharmaceutically acceptable salt thereof, and a pharmaceutically acceptable carrier. The pharmaceutical compositions of the invention can be employed to prevent the binding of a toxin or pathogen to a host cell. Thus, as described below, the pharmaceutical compositions can be administered to prevent infection, i.e., of a host cell or host animal, or as an antidote or prophylactic against, e.g., toxicity of a toxin which binds to a glycolipid, or a pathogen which binds to a glycolipid. Thus, the invention provides methods of treating conditions such as bacterial, fungal, or viral infections, by inhibiting attachment of a pathogen to a cell. Administration of a compound of the invention can also provide symptomatic relief of conditions caused by the presence of a toxin, e.g., a bacterial toxin, in the body of a subject.

In yet another embodiment, the invention provides a method for preparing a glycolipid mimic having a rigid hydrophobic moiety. The method includes the steps of providing a glycolipid or glycolipid analog having at least one functional group capable of being coupled with a rigid hydrophobic moiety, and coupling the glycolipid or glycolipid analog with a rigid hydrophobi moiety, thereby preparing the glycolipid mimic having a rigid hydrophobic moiety.

In still another aspect, the invention provides a method for inhibiting the binding of a toxin or a pathogen to a host cell. The method includes the step of contacting the toxin or pathogen, or the host cell, with a glycolipid mimic of the invention in an amount sufficient to inhibit the binding of the toxin or pathogen to the host cell, thereby inhibiting the binding of the toxin or pathogen to the host cell. The method includes the further step of contacting the host cell with the toxin or pathogen. The method is useful for inhibiting the binding of a toxin or pathogen to a host cell either in vitro or in vivo. In certain preferred embodiments, the pathogen is selected from the group consisting of bacterial, fungi, and viruses. In certain embodiments, the toxin is verotoxin.

It is believed that galactosylceramide is a receptor for HIV gp120. Accordingly, in a preferred embodiment, the glycolipid mimic is selected to retain a binding affinity for HIV gp120. In this embodiment, the saccharide portion of the glycolipid mimic is preferably comprises a galactosyl moiety.

The step of contacting the toxin, pathogen, or host cell can occur in vitro or in vivo, e.g., by administering a glycolipid mimic of the invention to a subject, e.g., an animal, e.g., a mammal, e.g., a human. As described in more detail below, the subject glycolipid mimics can be formulated into pharmaceutical compositions, which can be administered, e.g., to a human or animal subject, according to methods known in the art.

In another aspect, the invention provides a method of treating a bacterial (or viral or fungal) infection. In one embodiment, the method comprises administering to a subject in need thereof (i.e., a subject suffering from bacterial infection) an effective amount of a glycolipid mimic of the invention, such that the bacterial (or fungal or viral) infection is treated.

In yet another aspect, the invention provides a method for detecting the presence or absence of a pathogen or a toxin in a sample. The method includes the steps of contacting the sample with a glycolipid mimic of the invention, and measuring the binding of a pathogen or toxin, if present, to the glycolipid mimic, thereby detecting the presence or absence of the pathogen or toxin. In certain preferred embodiments, the glycolipid mimic is immobilized to a solid support. In certain preferred embodiments, the pathogen is selected from the group consisting of bacterial, fungi, and viruses.

Methods of detecting bound toxins or pathogens are known in the art, and are described, e.g., in U.S. Pat. Nos. 4,859,769, 5,449,608, 5,242,800 to Jimenez et al., and 5,164,298, and B. Boyd et al., *Eur. J Biochem.* 223:873–878 (1994).

In still another embodiment, the invention provides a method for isolating components of a pathogen which mediate pathogen attachment to a host cell. The method includes the steps of contacting a sample containing a pathogen (or a component of a pathogen) with a glycolipid mimic of the invention, and isolating a component of the pathogen which binds to the glycolipid mimic, such that a component of the pathogen which mediates pathogen attachment to a host cell is isolated. In a preferred embodiment, the glycolipid mimic is immobilized to a solid support. In certain preferred embodiments, the pathogen is selected from the group consisting of bacteria, fungi, and viruses.

Pharmaceutical compositions

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a glycolipid mimic of the present 35 invention which is effective for producing some desired therapeutic effect in at least a sub-population of cells in an animal and thereby blocking the biological consequences of, e.g., toxin or pathogen binding of the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present glycolipid mimics may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the glycolipid mimic which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a glycolipid mimic of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A glycolipid mimic of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered glycolipid mimic moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active glycolipid mimic, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active peptidomimetic.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a glycolipid mimic of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active glycolipid mimic of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the peptidomimetic in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more glycolipid mimics of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formnulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject glycolipid mimics in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These glycolipid mimics may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular glycolipid mimics of the present invention employed, or the ester, salt or amide thereof, the route of administration, the time of administration, the rate of excretion of the particular compound being employed, the duration of the treatment, other drugs, compounds and/or materials used in combination with the particular peptidomimetic employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a glycolipid mimic of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active glycolipid mimic may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

Exemplification

We now describe a new method for the oxidative cleavage of the sphingosine double bond within labile glycolipids, using limited amounts of $KMnO_4$ in a neutral aqueous tert-butanol solvent system, wherein the manganese dioxide formed during the course of the oxidation reaction is regenerated with $NaIO_4$ (see Examples).

The oxidation of the sphingosine double bond of GSLs was first investigated by Hakomori and coworkers using ozone in dichloromethane (10) or potassium permanganate/crown-ether complex in benzene (12) as oxidants. Permanganate oxidations have been carried out with methoxysialyl per-O-acetyl hematoside using 20 mg of unprotected GSL as starting precursor. Our attempts to employ the $KMnO_4$/crown-ether-benzene system to oxidize deN-aceyl GSLs, deacylglobotriaosyl ceramide (lyso-$Gb_3$) or deacylgalactosyl ceramide (lyso-Galcer or phycosine) with the amine group protected as N-acetyl (NAc), N-trifluoroacetyl (NTfa), N-trichloroacetyl (NTca) or N,N-dimethyl ($NMe_2$), and the hydroxyl groups protected as O-acetyl or O-benzoate derivatives, yielded the corresponding carboxylic acids in less than 5% yield.

The carboxylate group resulting from such oxidations has been coupled to an amine finctionality of a stationary support, and the immobilized glycan used in the affinity purification of antibodies produced against a given GSL (10, 11). Such immobilized glycosphingolipids are also useful in the investigation of their interaction with cell surface and purification of glycosylhydrolases or transferases. In addition, the carboxylate functionality of the oxidized GSL can be coupled to proteins to yield neoglycoproteins, or coupled to tailor-made polymers to yield multivalent high affinity glycopolymers. Although several synthetic organic schemes are known in the art for the the making of such glycoforms, they generally require the synthesis of oligosaccharide precursors containing suitable functionalities for polymerization and/or coupling. Availability of a facile oxidative cleavage of the sphingosine double bond of deacyl GSLs, as porvided herein, should avoid the need for synthesizing a glycan precursor, and therefore, provide a quick route to transform a naturally occurring GSL into the corresponding neoglycoconjugate.

EXPERIMENTAL SECTION

Solvents—dichlomethane (DCM), tert-butyl alcohol ($^t$BuOH), iso-propyl alcohol ($^{iso}$PrOH), 1,2-dichloro ethane (DCE), pyridine (Py), tetrahydrofuran (THF), diethyl ether ($Et_2O$), ethyl acetate (EtAc), benzene, methanol and chloroform—were purchased from either Caliden or Aldrich and ethanol from Commercial Alcohols, Inc., Brampton, Ontario. Other reagents were purchased from the following suppliers: Caliden; dicyclohexacarbodiimide (DCC), N-hydroxysuccinamide (NHS), trifluoroacetic anhydride, $K_2CO_3$; 2-adamantanamine hydrochloride (2$AdaNH_2$), 1-adamantanacetic acid (1AdaAcOH), sodium cyanoborohydride ($NaBH_3CN$), triethylamine ($Et_3N$); Aldrich: dicyclohexy-18-crown-6, 1-adamantanamine (1$AdaNH_2$), 9-amino-1,2,3,4-tetrahydroacridine hydrochloride hydrate ($AcrNH_2$), aniline (PhNH2), 37% aqueous formalin solution, 0.5N $H_2SO_4$ solution, trichloroacetic anhydride, acetic anhydride; BDH; ANALAR $KMnO_4$, ANALAR $HaHSO_3$; Pierce Chemical; 1-ethyl-3-(3-dimethyl aminopropyl) carbodiimide hydrochloride (EDC), Sulfo N-hydeoxysuccinimide (NHS-$SO_3$) and Fisher Scientific; meta-$NaIO_4$. Chromatographic materials—Silica gel, TLC, HPTLC, PrepTLC—were supplied by Caliden. Reverse phase C-18 cartridges were obtained from Waters and molecular sieves, 4Å from Fisher.

Solvents were dried by storing over activated (~120° C. for 16 hours) molecular sieves. THF was further purified by distillation under a nitrogen atmosphere. Crown ether (10 g) was recrystallized from hexane (4 to 5 mL) solution at –20° C., washed with cold (–20° C.) hexanes (1 mL) and dried at 40° C. under a stream of $N_2$. 2-adamantanamine hydrochloride, 1-adamantanamine and 9-amino-1,2,3,4-tetrahydroacridine hydrochloride hydrate were purified as follows: Amines (0.5 g) were desolved in $Et_2O$ (6 mL), washed twice with 0.5 M NaOH (1 mL portions) and then three times with distilled water (2 mL portions), the organic layer was dried over anhydrous $Na_2SO_4$, filtered and after stripping the $Et_2O$, the residue was redissolved in dry Py to give a known concentratoin and stored under $N_2$ atmosphere over 4Å sieves.

Globotriaosylceramide, $Gb_3$ was purified from human kidney according to known procedures. Galactocerebroside, GalCer was purchased from Sigma. DeN-acylated derivatives, lyso-$Gb_3$; phycosine, Lyso-GalCer were prepared by saponification at 100° C. with 1M methanolic NaOH.

EXAMPLE 1

Synthesis of N, N-Dimethylated Derivatives, $Gb_3NNMe_2$, $GalCerNNMe_2$

To a solution of 1 mg of deacylated GSL (approximately 2 µmol for disaccharide and 1.25 µmol for trisaccharide lyso-GSLs) in methanol (0.5 mL), 40 µL of 37% aqueous formaldehyde solution (15 mg formaldehyde, 500 µmol) and 100 µL of 0.32 M methanolic solution of $NaCNBH_3$ (prepared by dissolving 20 mg of $NaCNBH_3$ in 1 mL of dry MeOH) were added. After stirring the reaction mixture for 16 hours at room temperature (25° C.), methanol was removed under a flow of nitrogen and the remaining solid was then dissolved, with sonication, in 5 mL of distilled water. The resulting suspension was passed through a C-18 reverse phase cartridge, washed with 20 mL of water and the methylated product eluted with 20 mL of methanol. The yield of product was >90% by TLC. TLC showed that the methylated compound has a reduced mobility: for GalCer, the $R_f$ values for Lyso-GalCer and $GalCerNNMe_2$ are 0.80 and 0.75 (60 $ChCl_3$:35 MeOH:8 $H_2O$) or 0.38 and 0.31 (65 $CHCl_3$:25 MeOH:4 $H_2O$) respectively; for $Gb_3$.

EXAMPLE 2

Synthesis N-Acetyl Derivatives; $Gb_3NAc$, Galcer NAc, GalcerNTfa, and GalcerNTca Acylating reagents (N-acetylimidazole and N-trihalocetylimidazole) were prepared by adding solid imidazole (0.4 g, 6.0 mmol), divided in 3 portions, at 15 minutes intervals to a $CH_2Cl_2$(5 ml) solution of the corresponding anhydride, for example $(Cl_3CO)_2$(0.85 g, 2.7 mmol) at room temperature. The reaction mixture was stirred for 2 h and was assumed to be approximately a 0.5 M solution of the imidazole derivative.

The immidazole derivative was added to a $CH_2Cl_2$ suspension of deacyl-GSL (mg/mL), for example $GalcerNH_2$ (3 mg in 3 mL of $CH_2Cl_2$, 6 μmol) was added to N-trichloracetylimidazole solution (20 μL, 10 μmol), and the reaaction was monitored by TLC ($CHCl_3$:MeOH:$H_2O$;70:30:2). Once the deacyl-GSL was consumed, $CH_2Cl_2$ was removed under a stream of $N_2$ and a solution of $Et_3N$:MeOH:$H_2O$;2:6:10 (0.5 mL/mg of GSL) was added and incubated at 36° C. for 3 hours. The reaction was then diluted ten times with water, passed through a C-18 reverse phase cartridge, washed with $H_2O$ (5/mL/mg) and eluted with MeOH (10 mL/Mg). The yield by TLC was 90%.

EXAMPLE 3

Synthesis of Peracetylated Derivatives: $Gb_3(OAc)_{11}$, $Gb_3NAc(OAc)_{11}$ $Gb3NTfa(OAc)_{11}$, $Gb_3NTfa(OAc)_{11}$, $Gb_3NNMe_2(OAc)_{11}$, $GalCer(OAc)_5$, $GalCerNTfa(OAc)_5$, $GalCerNAc(OAc)_5$ and $GalCerNNMe_2(OAc)_5$:

Method A, suitable for the preparation of $NAc(OAc)_{11}$ derivatives. To a dried sample of lyso-GSL, a mixture of 1:2 acetic anhydride and pyridine (1 mL/1 mg of lyso-GSL) was added and incubated at 38° C. for 6 to 12 hours. The reaction was monitored by TLC using DCE-$^{iso}$PrOH, 80:15 as solvent system, and upon reaction completion, dried under a stream of $N_2$. Crude product was dissolved in DCM and loaded on to a 1.5×30 cm silica column (for a 5 mg scale reeaction). The column was eluted with a mixture of DCE-$^{iso}$PrOH, 20:1. It is noteworthy that the mobility of most of the peracetylated derivatives during column chromatography vary significantly with the degree of silica gel activation. Yield, >90% by TLC.

Method B, suitable for the preparation of $NNMe_2(OAc)_{11}$ and $NTfa(OAc)_{11}$ derivatives. To a dried sample of $NNMe_2$ or N-Tfa derivative, a 2:1 mixture of trifluoracetic anhydride-glacial acetic acid (1 mL/mg of glycolipid) was added and stirred at 25° C. for 3–6 hours. The remainder of the procedure was similar to method A. The solvent system for silica gel column chromatography for $N-Tfa(OAc)_{11}$ was DCM-EtAc 90:10. Yield, >80% by TLC.

EXAMPLE 4

Oxidation using $KMnO_4$/Crown Ether System

To a solution of dicyclohexyl-18-crown-6 in benzene (0.05M) was added an excess of $KMnO_4$ (approx. 20 mg) and sonicated for 15 minutes. The mixture was then centrifuged and the purple supernatant was assumed to contain approximately 0.005M solution of 1:1 adduct of $KMnO_4$•Crown-ether. This solution should be freshly prepared since it slowly depostis $MnO2$ upon standing.

Quenching solution was prepared by mixing 5 portions of $NaHSO_3$ (0.25M) solution and 1 portion $H_2SO_4$ (0.05N) or HCl.

EXAMPLE 5

Comparison Of the Oxidation Reactions of Galcer $(OAc)_5$ and $GalcerNAc(OAc)_5$ Using KMnO4 Crown-Ether System Method A:

An equimolar solution of the protected GSL precursors (0.5 mg, 1 μmol of $KMnO_4$) of oxidation solution and incubated at 36° C. for 1h. The initial clear purple reaction mixture appears a suspension of brown precipitate, suggesting most of the KMnO4 has been consumed. Equal aliquots (11 μL) were compared on an aluminum backed nano-silica TLC plate using two different solvent systems (DCE:$^{iso}$PPrOH; 85:15 and $CHCl_3$:MeOH::$H_2O$-0.4% $CaCl_2$•$2H_2O$;80:20:2). To the bulk reaction mixture aforementioned the procedure was repeated using 100 μL of oxidation solution for 1h and again using 50 μL of oxidation soution for 1h. For the second and third TLC comparison 12 μL and 12.5 μL of samples were used, respectively. At the end of third TLC, $MnO_2$ precipitate were separated from the benzene soluble material and the precipitates were dissolved in a 10:1 solution of 0.25M $NaHS)_3$: 1M HCL (0.5 mL).

To a benzene (150 μL) solution of protected glycolipid, ~0.6 μmol of the oxidation reagent was added (300 μL corresponds to approximately 75 μmol of $KMnO_4$) and stirred at 38° C. for 4 hours. However, if the purple color of the oxidant significantly diminished during the course of the reaction, further aliquots (50 μL) of $KMnO_4$ were added. Then 0.6 mL of quenching solution and 1 mL of water were added rapidly to give a clear colorless solution. If yellow color persisted, more of the quenching solution was added until a colorless solution was obtained. The aqueous phase was extracted twice with $Et_2O$ (3 mL portions) and the combined extracts were washed once with water (1 mL). Ether was removed under a stream of $N_2$.

Method B:

Oxidation Using $KMnO_4$/$^tBuOH$/$H_2O$/$NaIO_4$/$K_2CO_3$ system:

Reagent A is a 2:1 mixture of $^tBuOH$:$H_2O$. Solutions of $NaIO_4$ (0.4M), $K_2CO_3$ (0.25 M) and $KMnO_4$ (0.05 M).

Peracetylated glycolipid (0.6 μmol) was dissolved in $^tBuOH$/$H_2O$. Solutions of $NaIO_4$ (0.4 M), $K_2CO_3$(0.25 M) and $KMnO_4$ (0.05 M).

Peracetylated glycolipid (0.6 μmol) was dissolved in $^tBuOH$/$H_2O$ (600 μL) and $NaIO_4$ (25 μL, 10 μmol), $K_2CO_3$ (10 μL, 2.5 μmol) and $KMnO_4$ (20 μL, 1 mol) solutions were added in the given order and the resulting purple, turbid mixture was stirred at 38° C. for 4 hours. If clear peractylated derivatives were employed, the overall appearance of the reaction generally did not diminish during the course of the reaction. However, if diminishing purple color was observed with concomitant formation of brown $MnO_2$, additional aliquots (5 μL) of $KMnO_4$ solution were added. Quench solution (600 μL) was added and the remainder of the procedure was as above.

Discussion

When $KmNO_4$/crown-ether/benzene system was employed, as described by Young et al., to oxidize a 1 mg quantity of N,N dimethylated O-peracetylated derivateive of deacyl-globotriaosylceramide, $Gb_3(OAc)_{11}NNMe_2$, only trace amounts of orcinol positive sugar species were found at the end of workup procedure. When we monitored the same reaction mixture every 15 minutes we found that the combined intensities of all the orcinol positive bands decreased with time. This suggests either the oxidized carboxylic acid derivative is either insoluble or there is significant decomposition during the course of the reaction. However, the fact that only small quantities (<5%) of product were isolated after the workup procedure is suggestive of decomposition.

During the course of oxidation involving $KMnO_4$·crown ether complex, copious amounts of precipitate is formed, primarily consisting of $MnO_2$. Decomposing the $MnO_2$ precipitate with acidified aqueous $NaHSO_3$ solution, extracting $Et_2O$ soluble components and analysing by TLC showed significant amounts-approximately ⅓ of the precursor-sugar containing species. In the case $Galsph(OAc)_5NAc$ oxidation, most of the entrapped material was the carboxylate derivative, $Gal(OAc)_5NAcCOOH$.

It was also noted that if the required amount of $KMnO_4$·crown ether complex was added in portions (for example ⅓ portions at 30 minutes intervals) until approximately 30% of the substrate was consumed, the reaction proceeded in a controlled fashion. Upon further addition, multiple products appeared, probably due to the accumulation of $MnO_2$. This suggests that limiting the amount of $KMnO_4$ may significantly decrease the degree of decomposition.

EXAMPLE 6

Synthesis of Glvcolipid Mimics

Figure 1:
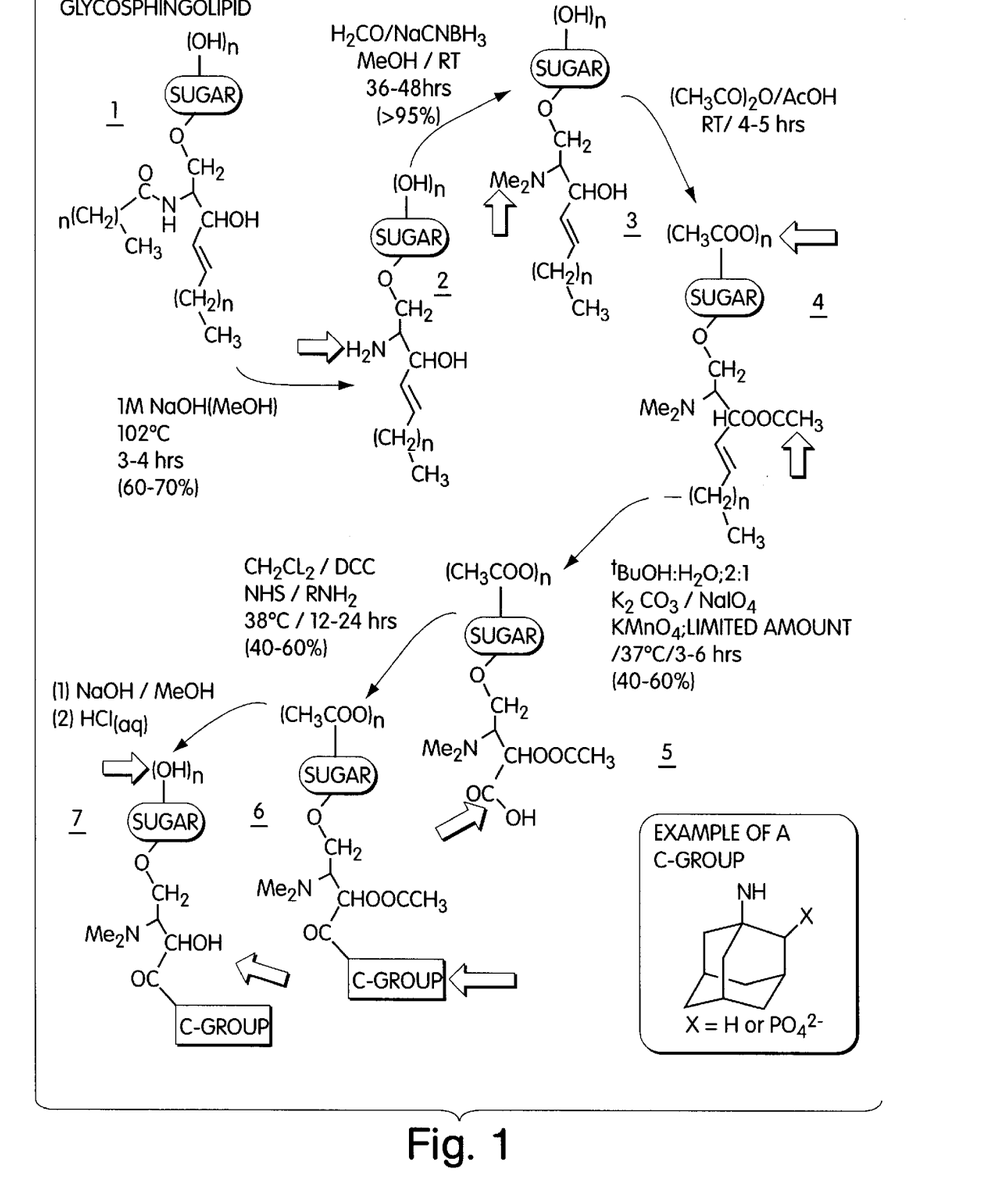
FIG. 1 is a reaction scheme showing a synthesis of certain of the compounds of the invention.
Figure 2:
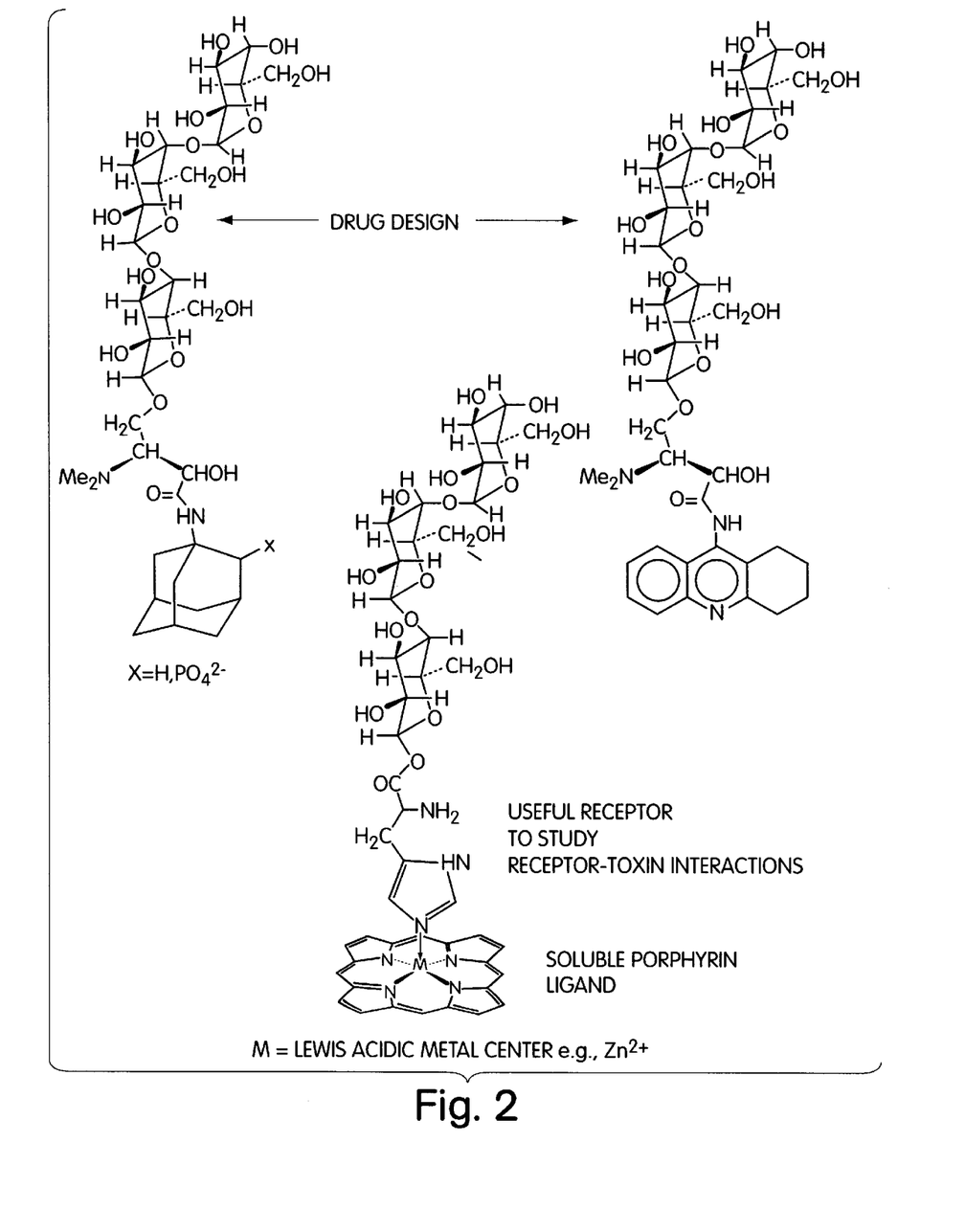
FIG. 2 shows certain selected compounds of the invention.
Figure 3A:
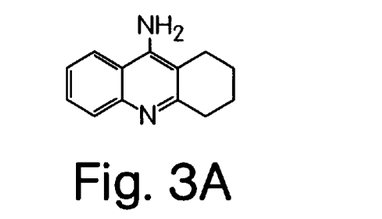
FIGS. 3A–3E show moieties which can be employed as rigid hydrophobic moieties in the compounds of the invention.
Figure 3B:
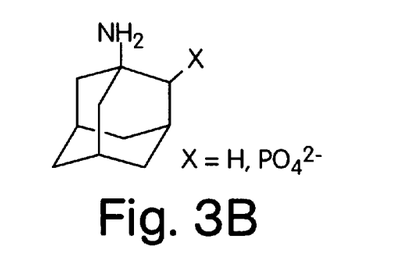
Figure 3C:
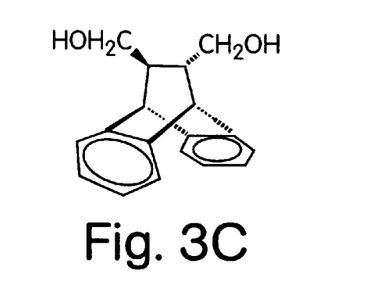
Figure 3D:
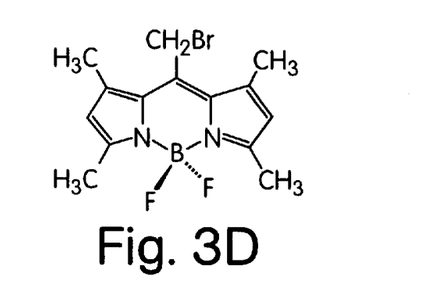
Figure 3E:
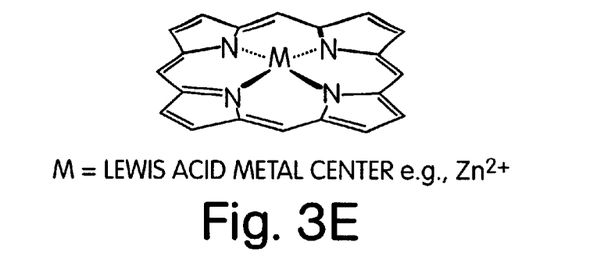

Method A:

The synthesis of several glycolipid mimic was performed according to the geeneral procedure outlined in FIG. 1.

As shown in FIG. 1, the glycosphingolipid 1 was first deacylated by saponification to yield the deacyl derivative 2 (the hollow arrows indicate the changed functionality of the molecule). Deacyl derivative 2 was then alkylated (e.g., by reductive amination as described above in Example 1) to yield diamino compound 3. Peracylation of the hydroxyl groups of 3 (e.g., with acetic anhydride) yielded 4, which was cleanly oxidized to 5 as described in Example 5, method B, above.

The hydrophobic moiety (C) was then coupled to the free carboxylate group of 5 under standard conditions. For example, carbodiimide-promoted coupling of 1-adamantaneamine with the carboxylate of the oxidized GSL 5 (DCC, N-hydroxysuccinimide (NHS)) produced the acetylated glycolipid mimic 6 in good yield. Deacylation of 6 yielded the glycolipid mimic 7.

Figure 4A:
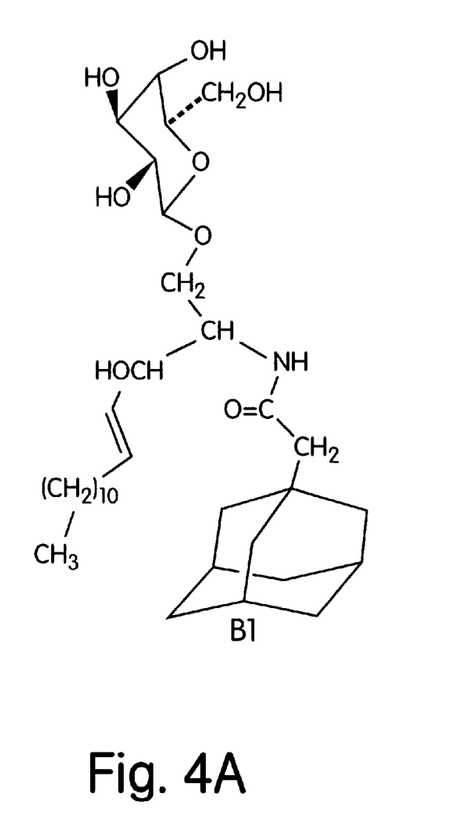
FIGS. 4A, 4B, 5A, and 5B show certain compounds of the invention.
Figure 4B:
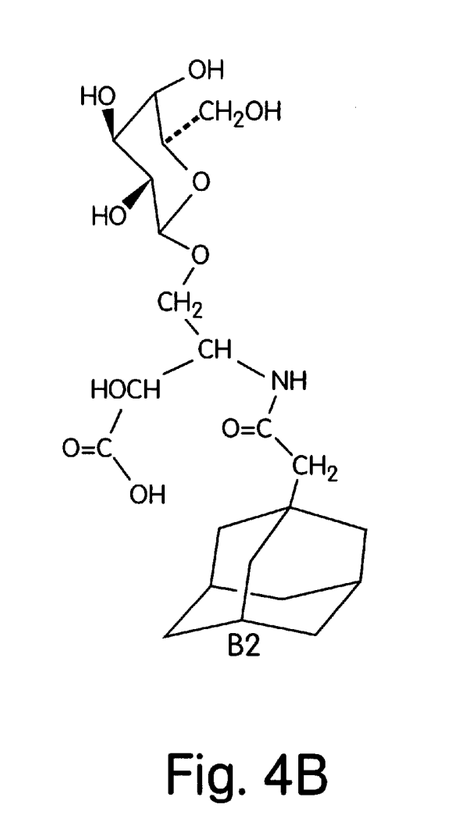

Method B:

Glycolipid analogs in which the hydrophobic moiety is linked to the amino group of the ceramide moiety are shown in FIG. 4. These compounds were made using galactosylceramide as starting material. Compound B 1 was prepared by deacylation of galactosylceramide, followed by acylation with 1-adamantanacetic acid in the presence of a coupling agent (e.g., DCC, NHS). Compound B2 was similarly prepared, except that the olefinic bond was cleaved by oxidation as previously described (Example 5, Method B) to yield the carboxylate (sugar hydroxyls were acylated, where necessary, to prevent oxidative cleavage).

EXAMPLE 7

Inhibition of Verotoxin Binding with $Gb_3$-derived Glycolipid Mimics

Glycolipid mimics prepared in Example 6, above, were tested to determine the effect of the mimics on verotoxin binding to $Gb_3$. The assay was performed according to the method described in B. Boyd et al., *Eur. J. Biochem.* 223:873–878 (1994). Verotoxin 1B subunit (VT1B) was used as a positive control to compete with the radiolabelled verotoxin 1. Free globotriaose oligosaccharide (i.e., the sugar moiety of $Gb_3$, shown in FIG. 5C as "$Gb_3$-sugar") was also tested.

Figure 5A:
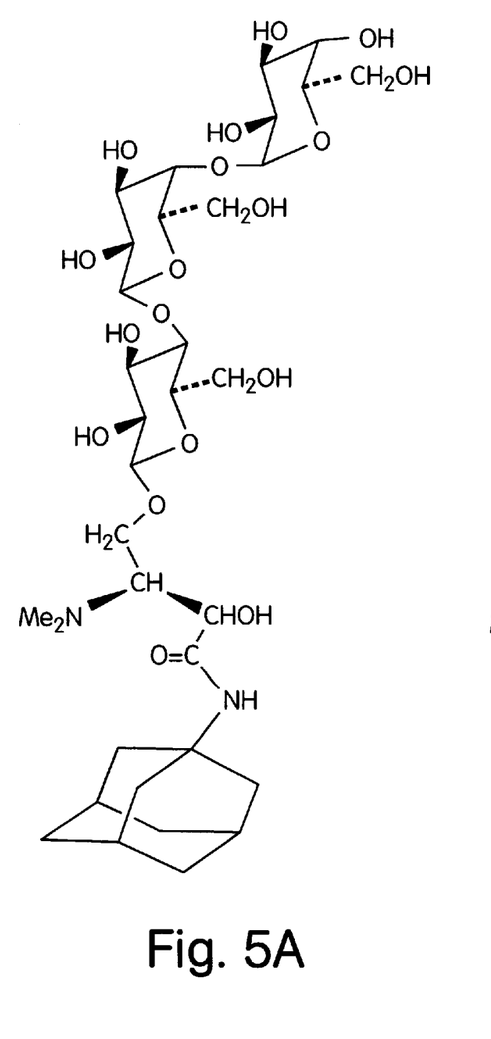
Figure 5B:
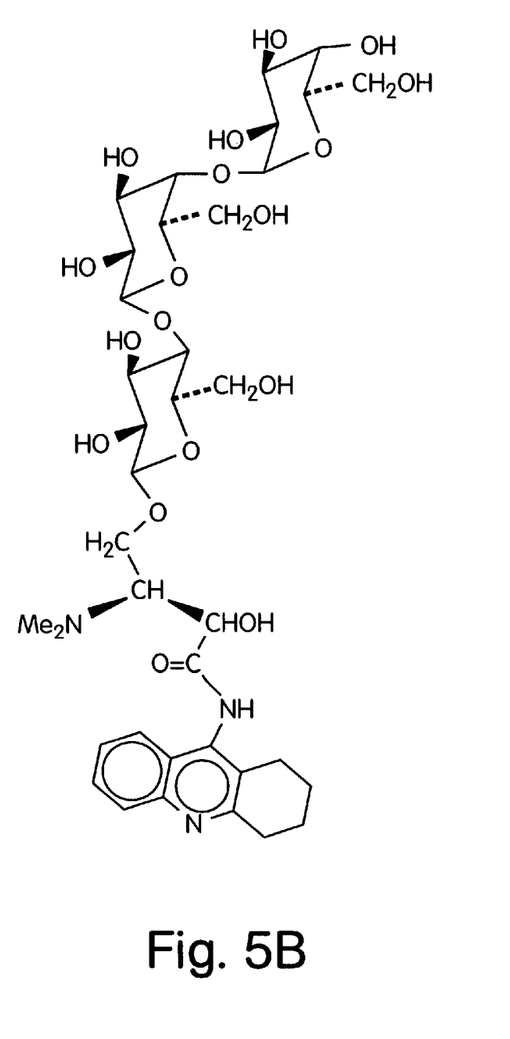
Figure 5C:
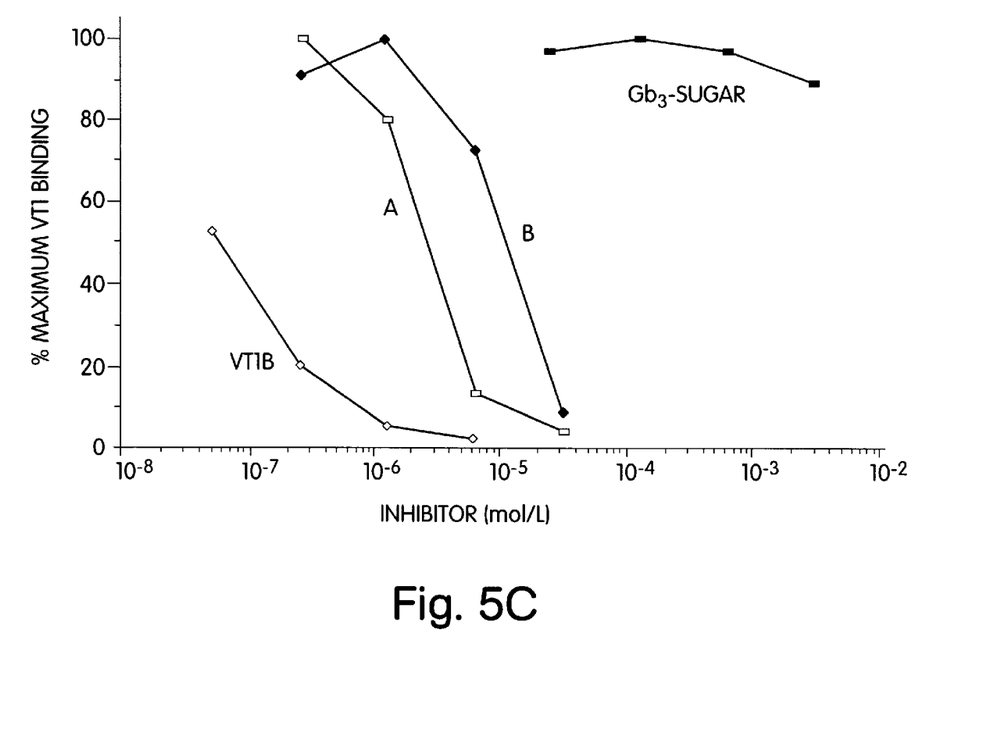
FIG. 5C is a graph showing the inhibition of binding of verotoxin to $Gb_3$ in the absence and presence of certain compounds of the invention.

As shown in FIG. 5C, VT1B shows strong inhibition of verotoxin binding, as expected. In contrast, $Gb_3$-sugar shows virtually no inhibition of verotoxin binding. Compounds A and B (prepared as in Example 6, Method A; and structures shown in FIGS. 5A and 5B) both demonstrated effective inhibition of verotoxin binding.

Compound A: Prepared as shown in FIG. 1. Sugar=$Gb_3$-sugar; C-group=1-adamantanamine.

Compound B: Prepared as shown in FIG. 1. Sugar=$Gb_3$-sugar; C-group=9-amino-1,2,3,4-tetrahydroacridine.

EXAMPLE 8

Inhibition of Verotoxin Binding: N-Acylated Glycolipid Mimics

Figure 6A:
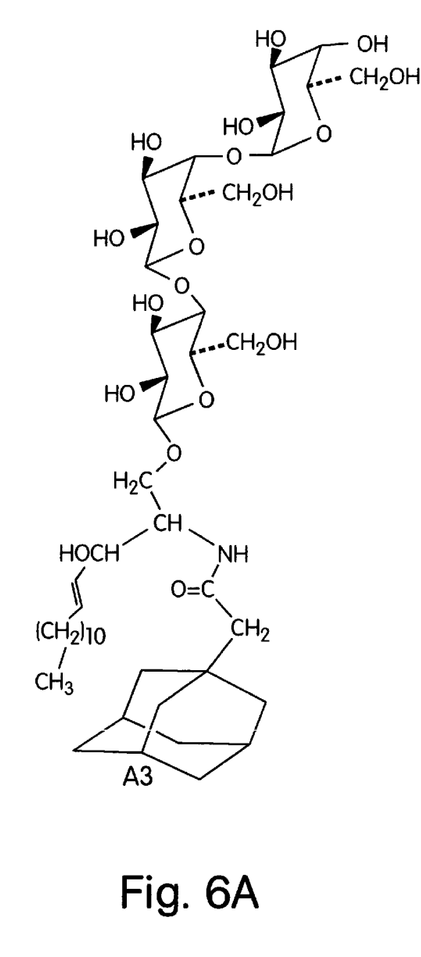
FIG. 6A shows the structure of compound A3.

Glycolipid mimics having a hydrophobic group linked to the amino group of the ceramide moiety were tested to determine the effect on verotoxin binding to $Gb_3$. The assay was performed by spectrophotometric detection of the amount of verotoxin bound to the $Gb_3$. Ph-1 is a neutralizing anti-VT1 antibody used as a positive control. The structure of compound A3 is shown in FIG. 6A. Compounds B1 and B2 were made as described in Example 6; compounds A1 and A3 were made by the procedure of Example 6, Method B, except that the starting material was $Gb_3$ rather than galactosylceramide. Surprisingly, compound A3 is highly water-soluble (A3 is not extracted into ether from water). Compound A1 was made by oxidative cleavage of the olefinic bond of compound A3 (to yield the corresponding carboxylate), as described in Example 5, Method B, above. Thus, compounds A3 and B1 differ only in the sugar moiety ($Gb_3$-sugar and galactosyl, respectively); and compounds A1 and B2 also differ only in the sugar moiety ($Gb_3$-sugar and galactosyl, respectively).

Figure 6B:
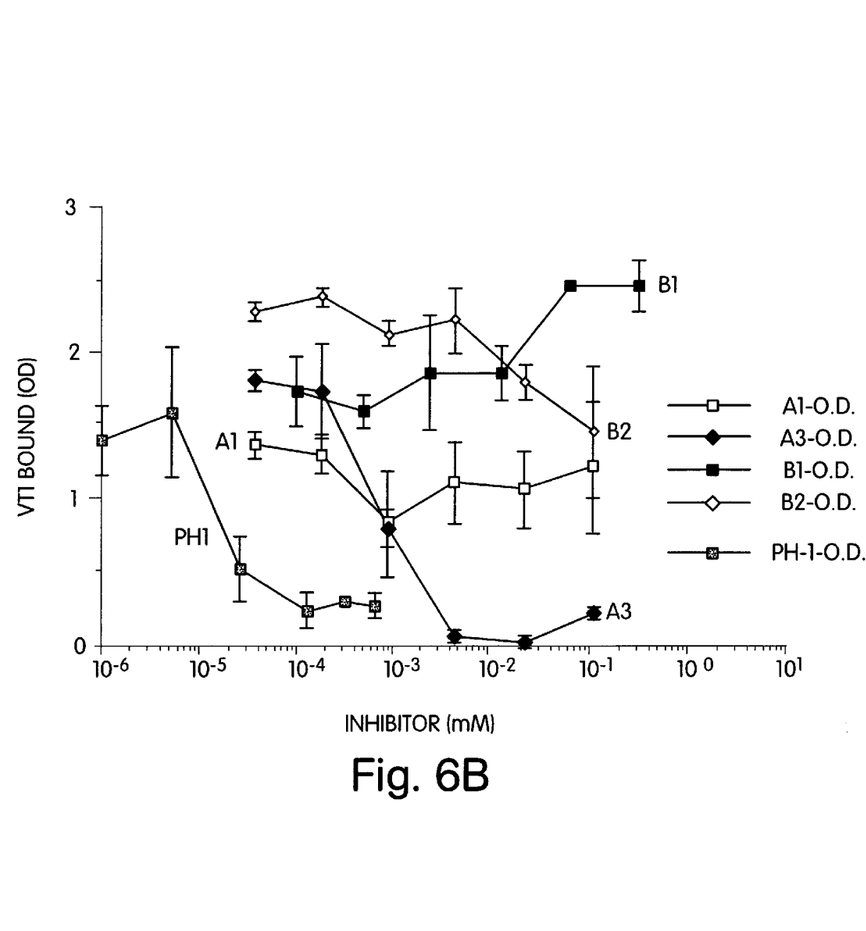
FIG. 6B is a graph showing the inhibition of binding of verotoxin to $Gb_3$ in the absence and presence of certain compounds of the invention.

The results of the inhibition assay are shown in FIG. 6B. The positive control inhibits binding of verotoxin to $Gb_3$, as expected. Compound A3 is also an effective water-soluble inhibitor of binding. However, compounds A1, B1, and B2 do not appear to be effective inhibitors under these conditions. The inactivity of compounds B1 and B2 is not surprising, as these compounds do not include the preferred saccharide moiety recognized by verotoxin.

REFERENCES

1. Fenderson, B. A., E. M. Eddy and S.-I. Hakomori. 1990. Glycoconjugate expression during embryogenesis and its biological significance. *BioEssays*. 12:173–179.
2. Hakomori, S. and R. Kannagi. 1983. Glycosphingolipids as tumor associated differentiation markers. *J. Natl. Can. Inst.* 71:231–251.
3. S.-I. Hakomori. 1990. Bifunctional role of glycosphingolipids. *J. Biol. Chem.* 265:18713–18716.
4. Sonnino, S., G. Kirschner, R. Ghidoni, D. Aquotti and G. Tettamanti. 1985. Preparation of GM1 ganglioside molecular species having homogeneous fatty acid and long chain base moieties. *J Lip Res.* 26:248–257.
5. Kiarash, A., B. Boyd and C. A. Lingwood. 1994. Glycosphingolipid receptor function is modified by fatty acid content: Verotoxin 1 and Verotoxin 1 and Verotoxin 2c preferentially recognize different globotriaosyl cceramide fatty acid homologues. *J. Biol Chem.* 269:11138–11146.
6. Pellizzari, A., H. Pang and C. A. Lingwood. 1992. Binding of verocytotoxin 1 to its receptor is influenced by differences in receptor fatty acid content. *Biochem.* 31:1363–1370.
7. Sakac, D., M. Zachos and C. A. Lingwood. 1992. Purification of the testicular galactolipid 3' phosphoadenosine 5' phosphosulfate fulfotransferase. *J Biol Chem.* 267:1655–1659.
8. Lingwood, C., and T. Taylor. 1986. Synthesis and use of galactolipid sulfotransferase substrate-analogue affinity probes. *Biochem Cell Biol.* 64:631–637.
9. Pagano, R. and 0. Martin. 1988. A series of fluorescent N-acylsphingosines: synthesis, physical properties and studies on cultured cells. *Biochem.* 27:4439–4445.
10. Laine, R., G. Yogeeswaren and S.-I. Hakomori. 1974. Glycosphingolipids covalently linked to agarose gel or glass beads. *J. Biol Chem* 14:4460–4466.
11. Kundu, S. K. and S. K. Roy. 1979. Aminopropyl silica gel as a solid support for preparation of glycolipid immunoadsorbent and purification of antibodies. *J Lipid Res.* 20:
12. MacDonald, D. L., P. L. and S. I. Hakomori. 1980. Notes on improved procedure for the chemical modification and degradation of glycosphinglipids. *J Lipid Res.* 21:642–645.

Those skilled in the art will recognize, or be able to ascertain using no more than routine experimentation, numerous equivalents to the specific procedures described herein. Such equivalents are considered to be within the scope of this invention and are covered by the following claims.

The contents of all patents and publications cited herein are hereby incorporated by reference.

Other embodiments are within the following claims.

What is claimed is:

1. A soluble glycolipid mimic represented by the formula A-B-C, in which A is a saccharide moiety; B is a linker moiety, and C is a rigid hydrophobic moiety, wherein said saccharide moiety retains at least one binding characteristic of a membrane bound glycolipid.

2. The glycolipid mimic of claim 1, wherein C is adamantanyl.

3. The glycolipid mimic of claim 1, wherein A is Gal (alpha 1–4)Gal(beta 1–4)Glc-1-, and wherein Gal is galactose and Glc is glucose.

4. The glycolipid mimic of claim 1, wherein C is acridinyl, benzopyrenyl, napthyl, tetrahydroacrinidinyl, anthracenyl, or a porphyrin.

5. The glycolipid mimic of claim 4, wherein C is 1,2,3,4-tetrahydroacridin-9-yl.

6. The glycolipid mimic of claim 1, wherein B is a fragment of a glycolipid.

7. The glycolipid mimic of claim 6, wherein B is —$CH_2$—CH($NMe_2$)—CH(OH)—C(O)NH—.

8. The glycolipid mimic of claim 6, wherein B—C is —$CH_2$—CH(NHC(O)$CH_2$R)—CH(OH)-trans-HC=CH—$(CH_2)_{10}CH_3$, wherein R is a rigid hydrophobic moiety.

9. The glycolipid mimic of claim 1, wherein said mimic is of the formula:A-B-C-D, wherein D is a carrier moiety.

10. The glycolipid mimic of claim 9, wherein D promotes an immunogenic response to the glycolipid.

11. The glycolipid mimic of claim 9, wherein D is a solid support or a linker to a solid support.

* * * * *